US000001942H

(19) United States

(12) Statutory Invention Registration

Theodoridis et al.

(10) Reg. No.: US H1942 H

(43) Published: Feb. 6, 2001

(54) HERBICIDAL 3-(PYRAZOLYLPHENYL) PROPANOIC ACIDS AND DERIVATIVES

(75) Inventors: George Theodoridis, Princeton; Scott D. Crawford, Bordentown; Lester L. Maravetz, Westfield, all of NJ (US)

(73) Assignee: FMC Corporation, Philadelphia, PA (US)

(21) Appl. No.: 09/144,773

(22) Filed: Sep. 1, 1998

(51) Int. Cl.[7] ..... C07D 231/04

(52) U.S. Cl. ..... 548/369.4; 548/371.1; 548/370.1

*Primary Examiner*—Charles T. Jordan
*Assistant Examiner*—Aileen J. Baker
(74) *Attorney, Agent, or Firm*—Donald J. Silvert; I. Robert Silverman

(57) ABSTRACT

Novel herbicidal compounds, compositions containing them, and methods for their preparation and use in controlling weeds are disclosed. The novel herbicidal compounds are 3-(pyrazolylphenyl)propanoic acids and derivatives having the formula:

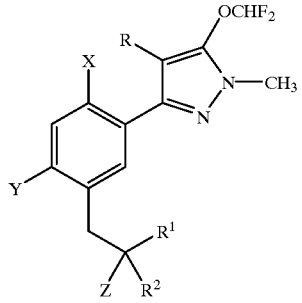

wherein X is H or halogen; Y is halogen, trihaloalkyl or cyano; Z and R are halogen; $R^1$ is carboxyl or agriculturally acceptable salt thereof, cyano, alkoxycarbonyl, alkylthiocarbonyl, alkoxyalkoxycarbonyl, aminocarbonyl, alkylaminocarbonyl, dialkylaminocarbonyl, or alkylsulfonylaminocarbonyl; and $R^2$ is hydrogen or lower alkyl.

13 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

HERBICIDAL 3-(PYRAZOLYLPHENYL) PROPANOIC ACIDS AND DERIVATIVES

BACKGROUND OF THE INVENTION

The present invention relates generally to novel herbicidal compounds and methods for their use in controlling unwanted plant species in agriculture. In particular, the present invention relates to novel 3-(pyrazolylphenyl) propanoic acids and derivatives and their use as herbicides.

There is a continuing demand for new herbicides. Herbicides are useful for controlling unwanted vegetation which may otherwise cause significant damage to crops such as wheat, corn, soybeans and cotton, to name a few. For crop protection, so-called "selective" herbicides are desired which can control the weeds without damaging the crop. Such crops are said to exhibit tolerance to the herbicide. In certain other situations, it is desirable to use herbicides that provide complete vegetation control such as in areas around railroad tracks and other structures. While many commercial products are available that provide selective or complete vegetation control, the demand exists for new, safe herbicides that are more effective and less costly.

German Patent Application 4419517-A1 discloses, among others, the following compound having herbicidal activity:

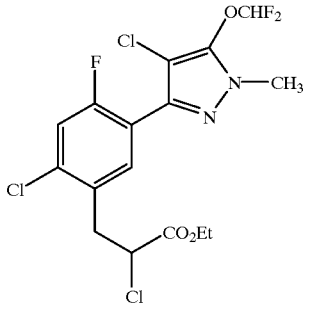

SUMMARY OF THE INVENTION

It has now been discovered that certain 3-(pyrazolylphenyl)propanoic acids and derivatives of formula I below have good activity as pre- and post-emergence herbicides. In particular, certain compounds of the present invention exhibit varying levels of selectivity favorable to soybean, corn or wheat in pre- or post-emergence applications. Certain compounds of the present invention are especially useful as pre-emergence herbicides for soybean and corn and as postemergence herbicides for wheat.

DETAILED DESCRIPTION OF THE INVENTION

The novel herbicidal 3-(pyrazolylphenyl)propanoic acids and derivatives of the present invention have the following formula:

I

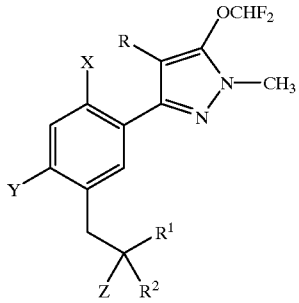

wherein X is H or halogen; Y is halogen, trihaloalkyl or cyano; Z and R are halogen; $R^1$ is carboxyl or agriculturally acceptable salt thereof, cyano, alkoxycarbonyl, alkylthiocarbonyl, alkoxyalkoxycarbonyl, aminocarbonyl, alkylaminocarbonyl, dialkylaminocarbonyl, or alkylsulfonylaminocarbonyl; and $R^2$ is hydrogen or lower alkyl.

Examples of agriculturally acceptable salts include, among others, the sodium, ammonium and trialkylammonium salts of compounds of formula I where $R^1$ is carboxyl. The term "alkyl" alone or as part of a larger moiety, includes straight or branched chain alkyl groups of 1 to 6 carbon atoms, while the term "alkoxy" alone or as part of a larger moiety, includes straight or branched chain alkoxy groups of 1 to 6 carbon atoms Preferred compounds are those of formula I wherein X is Cl or F; Y is Cl or Br; Z and R are Cl; $R^1$ is carboxyl or sodium, ammonium or trialkylammonium salt thereof, cyano, alkoxycarbonyl, alkylthiocarbonyl, alkoxyalkoxycarbonyl, aminocarbonyl, alkylaminocarbonyl, dialkylaminocarbonyl, or alkylsulfonylaminocarbonyl; and $R^2$ is H or methyl.

Particularly preferred compounds are those of formula I wherein X is Cl or F; Y is Cl; Z and R are Cl; $R^1$ is carboxyl or sodium, ammonium or trialkylammonium salt thereof, or alkoxycarbonyl; and $R^2$ is H.

Scheme 1 below illustrates a general route for preparing compounds of the present invention. The known β-ketoester II may be treated with methylhydrazine (step a) to form the hydroxypyrazole III. Alkylation of the OH group on the pyrazole ring of III with chlorodifluoromethane (step b) provides the corresponding difluoromethoxypyrazole IV. By treating IV with an N-halosuccinimide (step c), a halogen substituent may be introduced at the 4-position of the pyrazole ring (where the R group is attached) to give V. The aniline VII may be prepared in two steps (d and e) from V by nitration to give VI followed by reduction of the nitro group.

Using Meerwein reaction conditions (Scheme 1, step f), compounds of the present invention may be obtained by treating VII with a mixture of an alkyl nitrite; a copper (II) halide selected from $CuCl_2$ and $CuBr_2$; and an activated olefin selected from the group consisting of $CH_2{=}CHCO_2$-alkyl, $CH_2{=}C(CH_3)CO_2$-alkyl, $CH_2{=}CHCN$, and $CH_2{=}C(CH_3)CN$ in a suitable solvent. Examples of alkyl nitrites that may be used include isopentylnitrite and t-butylnitrite. Suitable solvents include polar, organic solvents such as acetonitrile and acetone. Thus, for example, when VII is treated with a mixture of copper(II) chloride, t-butylnitrite, and ethyl acrylate in acetonitrile, the target herbicidal compounds VIII are obtained.

Scheme I

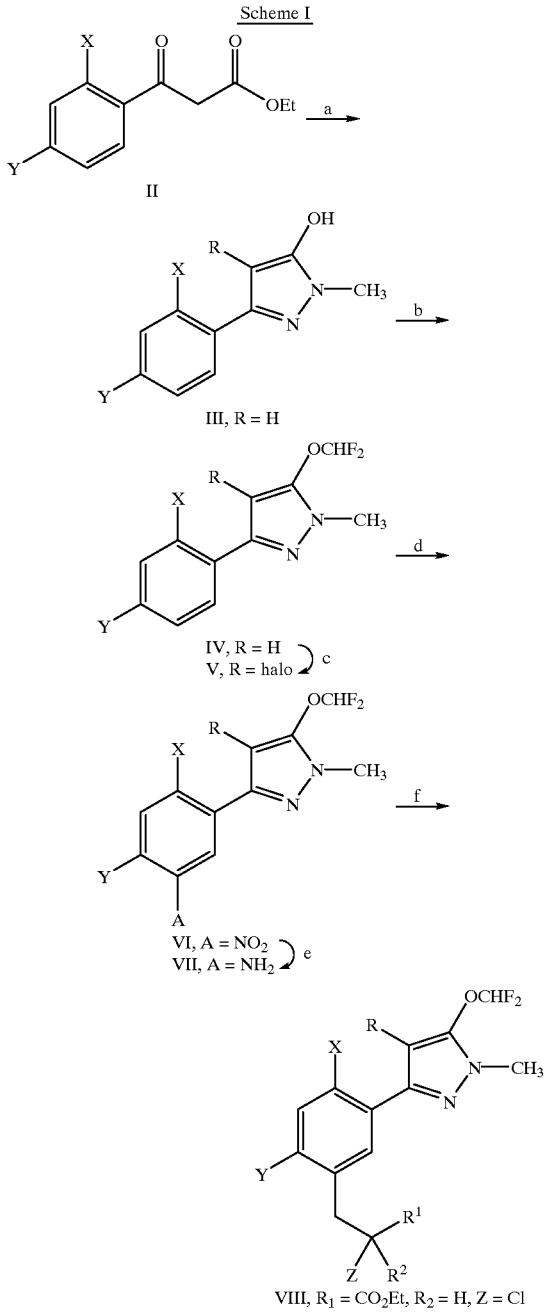

a) $NH_2NHCH_3$, isopropanol, reflux;
(b) $ClCHF_2$, $K_2CO_3$, DMF, 100° C.;
(c) N-halosuccinimide, DMF, room temperature;
(d) $HNO_3$, $H_2SO_4$, 0–10° C.;
(e) Fe, aq. HOAc;
(f) t-BuONO, $CH_2{=}CHCO_2Et$, $CuCl_2$, $CH_3CN$ By replacing the ethyl acrylate used in step (f) of Scheme 1 with other activated olefins other compounds of the present invention may be obtained. For example, compounds of formula I where $R^1$ is CN may be obtained according to Scheme 1 above, except that in step (f) $CH_2{=}CHCN$ is used in place of $CH_2{=}CHCO_2Et$. When $CH_2{=}C(CH_3)CO_2Et$ is used in place of $CH_2{=}CHCO_2Et$ in step (f), compounds of formula I where $R^2$ is $CH_3$ may be obtained. Also, compounds of formula I where Z is Br may be obtained when $CuBr_2$ is used in place of $CuCl_2$ in step (f).

Further compounds of the present invention may be obtained from compounds of formula I where $R^1$ is an alkoxycarbonyl group (ester) by hydrolysis of the ester to give the corresponding carboxylic acid. Conversion of the resulting carboxylic acid to other esters and to salts and amides of the present invention may be carried out by methods that are well-known to one skilled in the art.

Compounds of the present invention may also be prepared in accordance with the procedures shown in the Examples below, by procedures analogous to those described above or shown in the Examples, or by other methods that are generally known or available to one skilled in the art.

SYNTHESIS EXAMPLES

SYNTHESIS OF ETHYL 2-CHLORO-3-[2-CHLORO-4-FLUORO-5-(4-CHLORO-5-DIFLUOROMETHOXY-1-METHYLPYRAZOL-3-YL)PHENYL]PROPANOATE

Step A Ethyl (2-fluoro-4-chlorophenyl)malonate

A stirred mixture of 72.0 grams (0.42 mole) of potassium ethyl malonate (prepared in the manner disclosed in Organic Synthesis, Coll. Vol. IV, 417 1963) in 300 mL of acetonitrile was cooled to 10–15° C. and 58.4 mL (0.42 mole) of triethylamine, followed by 53.1 grams (0.55 mole) of magnesium chloride, were added. Upon completion of addition, the reaction mixture was allowed to warm to 25° C. where it stirred for about 2.5 hours. After this time the reaction mixture was cooled to 0° C. and 40.9 grams (0.21 mole) of 2-fluoro-4-chlorobenzoyl chloride was added slowly, followed by an additional 4.5 grams (0.045 mole) of triethylamine. The reaction mixture was then warmed to 20–25° C. where it stirred for about 18 hours. After this time the reaction mixture was concentrated under reduced pressure to a residue which was dissolved in 100 mL toluene and again concentrated under reduced pressure. The residue was dissolved in a second 100 mL portion of toluene, and the solution was cooled to 10–15° C. To the cooled, stirred solution was slowly added 300 mL of aqueous 13% hydrochloric acid while maintaining the solution temperature at about 25° C. The organic layer was separated and washed with portions of aqueous 12% hydrochloric acid and water. The organic layer was concentrated under reduced pressure to a residue. The residue was subjected to column chromatography on silica gel using methylene chloride as the eluant. The product-containing fractions were combined and concentrated under reduced pressure, yielding about 44.0 grams of ethyl (2-fluoro-4-chlorophenyl)malonate.

Step B 1-Methyl-5-hydroxy-3-(2-fluoro-4-chlorophenyl) pyrazole

A stirred solution of 44.0 grams (0.18 mole) of ethyl (2-fluoro-4-chloro-phenyl)malonate and 9.6 grams (0.24 mole) of methylhydrazine in 150 mL of 2-propanol was heated at reflux for about 48 hours. After this time the reaction mixture was concentrated under reduced pressure to a residue. The residue was slurred in 80 mL of methylene chloride and filtered to collect 27.0 grams of 1-methyl-2-hydroxy-3-(2-fluoro-4-chlorophenyl)pyrazole.

Step C 1-Methyl-5-difluoromethoxy-3-(2-fluoro-4-chlorophenyl)pyrazole

A stirred solution of 23.5 grams (0.104 mole) of 1-methyl-5-hydroxy-3-(2-fluoro-4-chlorophenyl)pyrazole and 43.0 grams (0.312 mole) of potassium carbonate in about 600 mL of N,N-dimethylformamide was warmed to 100° C., and an excess of chlorodifluoromethane was bubbled in during a 75 minute period. The reaction mixture was allowed to cool to ambient temperature, then it was poured into about 1000 mL of water. The resultant mixture was neutralized with aqueous 2N hydrochloric acid and extracted with three portions of diethyl ether. The combined extracts were dried with magnesium sulfate and filtered. The filtrate was concentrated under reduced pressure to a residual oil. The oil was subjected to column chromatography on silica gel using methylene chloride as the eluant. The product-containing fractions were combined and concentrated under reduced pressure, yielding 16.5 grams of 1-methyl-5-difluoromethoxy-3-(2-fluoro-4-chlorophenyl)pyrazole. The NMR spectrum was consistent with the proposed structure.

Step D 1-Methyl-5-difluoromethoxy-4-chloro-3-(2-fluoro-4-chlorophenyl)pyrazole

A solution of 16.2 grams (0.059 mole) of 1-methyl-5-difluoromethoxy-3-(2-fluoro-4-chlorophenyl)pyrazole and 8.5 grams (0.064 mole) of N-chlorosuc-cinimide in about 500 mL of N,N-dimethylformamide was stirred at ambient temperature for about 18 hours. After this time the reaction mixture was poured into about 1600 mL of water and then extracted with two portions of diethyl ether. The combined extracts were washed with one portion of aqueous 10% lithium chloride and two portions of a saturated aqueous solution of sodium chloride. The organic layer was dried with magnesium sulfate and filtered. The filtrate was concentrated under reduced pressure, yielding 18.0 grams of 1-methyl-5-difluoromethoxy-4-chloro-3-(2-fluoro-4-chlorophenyl)pyrazole. The NMR spectrum was consistent with the proposed structure.

Step E 1-Methyl-5-difluoromethoxy-4-chloro-3-(2-fluoro-4-chloro-5-nitrophenyl)pyrazole A mixture of 18.0 grams (0.058 mole) of 1-methyl-5-difluoromethoxy-4-chloro-3-(2-fluoro-4-chlorophenyl) pyrazole and 120 mL of concentrated sulfuric acid was stirred, and when the pyrazole was dissolved, the solution was cooled to 0° C. To this was added dropwise 5.5 mL (0.074 mole) of 70% nitric acid at a rate to maintain the reaction mixture temperature below 3° C. Upon completion of addition the reaction mixture was allowed to warm to about 10° C. where it stirred for two hours. After this time the reaction mixture was poured into ice-water and then extracted with several portions of diethyl ether. The combined extracts were dried with magnesium sulfate and filtered. The filtrate was concentrated under reduced pressure, yielding 20.1 grams of 1-methyl-5-difluoromethoxy-4-chloro-3-(2-fluoro-4-chloro-5-nitrophenyl)pyrazole. The NMR spectrum was consistent with the proposed structure.

Step F 1-Methyl-5-difluoromethoxy-4-chloro-3-(2-fluoro-4-chloro-5-aminophenyl)pyrazole A stirred solution of 14.9 grams (0.042 mole) of 1-methyl-5-difluoromethoxy-4-chloro-3-(2-fluoro-4-chloro-5-nitrophenyl)pyrazole and 20 mL of water in 200 mL of acetic acid was warmed to 50° C., and 10.0 grams (0.179 mole) of iron powder was added portionwise. Upon completion of addition the reaction mixture was allowed to cool to ambient temperature. The reaction mixture was then poured into about 400 mL of a mixture of 1:1 ethyl acetate and water. The mixture was filtered through diatomaceous earth, and the organic layer in the filtrate was separated. The aqueous layer was washed with about 200 mL of ethyl acetate, and the wash was combined with the organic layer separated from the filtrate above. The combination was dried with magnesium sulfate and filtered. The filtrate was concentrated under reduced pressure to a residue. The residue was subjected to column chromatography on silica gel, using 5% methanol in methylene chloride as the eluant. The product-containing fractions were combined and concentrated under reduced pressure, yielding 12.2 grams of 1-methyl-5-difluoromethoxy-4-chloro-3-(2-fluoro-4-chloro-5-aminophenyl)pyrazole. The NMR spectrum was consistent with the proposed structure.

Step G Ethyl 2-chloro-3-[2-chloro-4-fluoro-5-(4-chloro-5-difluoromethoxy-1-methylpyrazol-3-yl)phenyl] propanoate A mixture of 0.55 gram (0.004 mole) of copper(II) chloride and 0.6 mL (0.005 mole) of tert-butyl nitrite in 7.0 mL of ethyl acrylate and 10 mL of acetonitrile was stirred for five minutes, and cooled to 15° C. With continued stirring, a solution of 1.0 gram (0.003 mole) of 1-methyl-5-difluoromethoxy-4-chloro-3-(2-fluoro-4-chloro-5-aminophenyl)pyrazole in about five mL of acetonitrile was added dropwise while maintaining the reaction mixture temperature below 30° C. Upon completion of addition the reaction mixture was stirred with continued cooling for ten minutes, then it was allowed to warm to ambient temperature where it stirred for 1.5 hours. After this time the reaction mixture was poured into 75 mL of aqueous 20% hydrochloric acid. The resultant mixture was extracted with two 50 mL portions of diethyl ether. The combined extracts were washed with one portion of aqueous 20% hydrochloric acid, then dried with magnesium sulfate. The mixture was filtered, and the filtrate was concentrated under reduced pressure to an oil residue. The residue was subjected to column chromatography on silica gel using methylene chloride as the eluant. The product-containing fractions were combined and concentrated under reduced pressure, yielding 0.9 gram of ethyl 2-chloro-3-[2-chloro-4-fluoro-5-(4-chloro-5-difluoromethoxy-1-methylpyrazol-3-yl)phenyl]propanoate. The NMR spectrum was consistent with the proposed structure.

TABLE 1

Derivatives of 2-Substituted-5-(5-difluoromethoxy-4-halo-1-methylpyrazol-3-yl)phenylpropanoic Acids

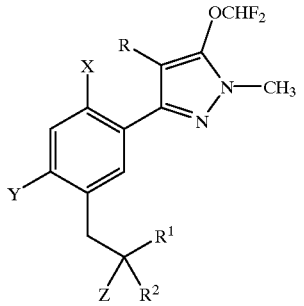

| Cmpd. No. | X | Y | Z | R | $R^1$ | $R^2$ |
|---|---|---|---|---|---|---|
| 1 | Cl | Cl | Cl | Cl | $CO_2CH_2CH_3$ | H |
| 2 | F | Cl | Cl | Cl | $CO_2CH_2CH_3$ | H |
| 3 | F | Cl | Cl | Cl | $C{=}O(SCH_3)$ | H |
| 4 | F | Cl | Cl | Cl | $C{=}O(SCH_2CH_3)$ | H |
| 5 | F | Cl | Cl | Cl | $CO_2CH_3$ | $CH_3$ |
| 6 | Cl | Cl | Cl | Cl | $CO_2CH_3$ | $CH_3$ |
| 7 | F | Br | Cl | Cl | $CO_2CH_3$ | H |
| 8 | F | Br | Cl | Cl | $CO_2CH_2CH_3$ | H |
| 9 | F | Cl | Cl | Br | $CO_2CH_2CH_3$ | H |
| 10 | F | Cl | Cl | Cl | $CO_2CH_3$ | H |
| 11 | F | Cl | Br | Cl | $CO_2CH_3$ | H |
| 12 | H | Cl | Cl | Cl | $CO_2CH_3$ | H |
| 13 | F | Cl | Cl | Cl | $CO_2H$ | H |
| 14 | F | Cl | Cl | Cl | $CO_2CH_2CH_2OCH_3$ | H |
| 15 | F | Cl | Cl | Cl | $CO_2CH(CH_3)_2$ | H |

TABLE 1-continued

Derivatives of 2-Substituted-5-(5-difluoromethoxy-4-halo-1-methylpyrazol-3-yl)phenylpropanoic Acids

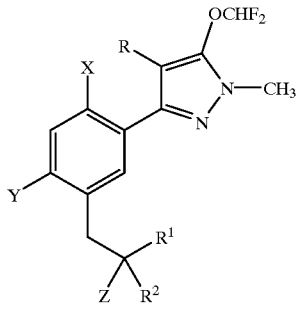

| Cmpd. No. | X | Y | Z | R | $R^1$ | $R^2$ |
|---|---|---|---|---|---|---|
| 16 | F | Cl | Cl | Cl | $CONH_2$ | H |
| 17 | F | Cl | Cl | Cl | $CONHCH_3$ | H |
| 18 | F | Cl | Cl | Cl | $CON(CH_3)_2$ | H |
| 19 | F | Cl | Cl | Cl | $CONHSO_2CH_3$ | H |
| 20 | F | Cl | Cl | Cl | $CO_2Na$ (salt) | H |
| 21 | F | Cl | Cl | Cl | $CO_2NH(CH_3)_3$ (salt) | H |
| 22 | F | Cl | Cl | Cl | $CO_2H$ | H |
| 23 | C | Cl | Cl | Cl | $CONH_2$ | H |
| 24 | C | Cl | Cl | Cl | $CO_2CH_2CH_2CH_3$ | H |
| 25 | C | Cl | Cl | Cl | $CO_2Na$ (salt) | H |
| 26 | F | CN | Cl | Cl | $CO_2CH_3$ | H |
| 27 | F | CN | Cl | Cl | $CO_2CH_2CH_3$ | H |
| 28 | C | CN | Cl | Cl | $CO_2CH_3$ | H |
| 29 | C | $CF_3$ | Cl | Cl | $CO_2CH_3$ | H |
| 30 | F | $CF_3$ | Cl | Cl | $CO_2CH_3$ | H |
| 31 | H | Cl | Cl | Cl | CN | H |
| 32 | C | Cl | Cl | Cl | CN | H |
| 33 | F | Cl | Cl | Cl | CN | H |
| 34 | F | Cl | Br | Cl | CN | H |
| 35 | F | Br | Cl | Cl | CN | H |
| 36 | F | CN | Cl | Cl | CN | H |
| 37 | F | $CF_3$ | Cl | Cl | CN | H |
| 38 | F | Cl | Cl | Br | CN | H |
| 39 | F | Cl | Cl | Br | CN | $CH_3$ |
| 40 | F | Cl | Cl | Cl | CN | $CH_3$ |
| 41 | F | Cl | Br | Cl | CN | $CH_3$ |
| 42 | Cl | Cl | Cl | Cl | CN | $CH_3$ |
| 43 | F | Cl | Cl | Cl | $CO_2NH_4$ (salt) | H |

HERBICIDAL ACTIVITY

The compounds of the present invention were tested for pre- and post-emergence herbicidal activity using a variety of crops and weeds. The test plants included soybean (Glycine max var. Winchester), field corn (*Zea mays* var. Pioneer 3732), wheat (*Triticum aestivum* var. Lew), morning glory (*Ipomea lacunosa* or *Ipomea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium strumarium* L.).

For pre-emergence testing, two disposable fiber flats (8 cm×15 cm×25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for post-emergence testing were prepared in the same manner except that they were planted 9–14 days prior to the pre-emergence flats and were placed in a greenhouse and watered, thus allowing the seeds to germinate and the foliage to develop.

In both pre- and post-emergence tests, a stock solution of the candidate herbicide was prepared by dissolving 0.27 g of the compound in 20 mL of water/acetone (50/50) containing 0.5% v/v sorbitan monolaurate. For an application rate of 3000 g/ha of herbicide a 10 mL portion of the stock solution was diluted with water/acetone (50/50) to 45 mL. The volumes of stock solution and diluent used to prepare solutions for lower application rates are shown in the following table:

| Application Rate (g/ha) | Volume of Stock Solution (mL) | Volume of Acetone/Water (mL) | Total Volume of Spray Solution (mL) |
|---|---|---|---|
| 3000 | 10 | 35 | 45 |
| 1000 | 3 | 42 | 45 |
| 300 | 1 | 44 | 45 |
| 100 | 0.3 | 45 | 45.3 |
| 30 | 0.1 | 45 | 45.1 |
| 10 | 0.03 | 45 | 45.03 |
| 3 | 0.01 | 45 | 45.01 |

The pre-emergence flats were initially subjected to a light water spray. The four flats were placed two by two along a conveyor belt (i.e., the two pre-emergence flats, followed by the two post-emergence flats). The conveyor belt fed under a spray nozzle mounted about ten inches above the post-emergent foliage. The pre-emergent flats were elevated on the belt so that the soil surface was at the same level below the spray nozzle as the foliage canopy of the post-emergent plants. After the spray of herbicidal solution was commenced and stabilized, the flats were passed under the spray at a speed to receive a coverage equivalent to 1000 L/ha. At this coverage, the application rates are those shown in the above table for the individual herbicidal solutions. The pre-emergence flats were watered immediately thereafter, placed in the greenhouse, and watered regularly at the soil surface. The post-emergence flats were immediately placed in the green-house, but not watered until 24 hours after treatment with the test solution. Thereafter, they were regularly watered at ground level. After 12–17 days, the plants were examined, and the phytotoxicity data were recorded.

Herbicidal activity data at selected application rates are given for various compounds of the present invention in Tables 2 and 3. The test compounds are identified by numbers which correspond to those in Table 1.

Phytotoxicity data are taken as percent control. Percent control is determined by a method similar to the 0 to 100 rating system disclosed in "Research Methods in Weed Science," $2^{nd}$ ed., B. Truelove, Ed. (Southern Weed Science Society; Auburn University, Auburn, Ala., 1977). The rating system is as follows:

| Rating (% Control) | Description of Main Categories | Crop Description | Weed Description |
|---|---|---|---|
| 0 | No effect | No crop reduction or injury | No weed control |
| 10 | Slight effect | Slight discoloration or stunting | Very poor weed control |
| 20 | | Some discoloration, stunting or stand loss | Poor weed control |
| 30 | | Crop injury more pronounced, but not lasting | Poor to deficient weed control |
| 40 | Moderate effect | Moderate injury, crop usually recovers | Deficient weed control |
| 50 | | Crop injury more lasting, recovery doubtful | Deficient to moderate weed control |
| 60 | | Lasting crop injury, no recovery | Moderate weed control |
| 70 | Severe | Heavy injury and stand loss | Control somewhat less than satisfactory |
| 80 | | Crop nearly destroyed, a few survivors | Satisfactory to good weed control |
| 90 | | Only occasional live plants left | Very good to excellent control |
| 100 | Complete effect | Complete crop destruction | Complete weed destruction |

TABLE 2

PREEMERGENCE HERBICIDAL ACTIVITY (% CONTROL at 1.0 kg/ha)

| | Compound No. | |
|---|---|---|
| Species | 1 | 2 |
| Soybean | 100 | 90 |
| Wheat | 20 | 30 |
| Corn | 40 | 10 |
| Velvetleaf | 100 | 100 |
| Morningglory | 100 | 100 |
| Chickweed | 100 | 100 |
| Cocklebur | 100 | 100 |
| Blackgrass | 40 | 50 |
| Green foxtail | 100 | 100 |
| Johnsongrass | 80 | 70 |

TABLE 3

POSTEMERGENCE HERBICIDAL ACTIVITY (% CONTROL at 1.0 kg/ha)

| | Compound No. | |
|---|---|---|
| Species | 1 | 2 |
| Soybean | 100 | 100 |
| Wheat | 30 | 55 |
| Corn | 60 | 90 |
| Chickweed | 100 | 100 |
| Cocklebur | 100 | 100 |
| Blackgrass | 40 | 60 |
| Green foxtail | 100 | 100 |
| Johnsongrass | 100 | 90 |

Herbicidal compositions are prepared by combining herbicidally effective amounts of the active compounds with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application. It is to be understood that the amounts specified in this specification are intended to be approximate only, as if the word "about" were placed in front of the amounts specified.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersant. The wettable powder is ultimately applied to the soil either as a dry dust or as an emulsion in water or other liquid. Typical carriers for wettable powders include Fuller's earth, kaolin clays, silicas, and other highly absorbent, readily wet inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.0 parts of the herbicidal compound, 17.9 parts of Palmetto clay, and 1.0 part of sodium lignosulfonate and 0.3 part of sulfonated aliphatic polyester as wetting agents. Additional wetting agent and/or oil will frequently be added to the tank mix for post-emergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isphorone, or other non-volatile organic solvents. For herbicidal application these concentrates are dispersed in water or other liquid carrier and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and will typically contain active ingredients in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. Surface-active agents, when used, normally comprise 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relative coarse particles, are of particular utility for aerial distribution or for penetration of cover crop canopy. Pressurized sprays, typically aerosols wherein the active ingredient is dispersed in finely divided form as a result of vaporization of a low boiling dispersant solvent carrier, such as the Freon fluorinated hydrocarbons, may also be used. Water-soluble or water-dispersible granules are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The active herbicidal compounds of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, e.g. about 1 to 250 g/ha, preferably about 4 to 30 g/ha. For field use, where there are losses of herbicide, higher application rates (e.g., four times the rates mentioned above) may be employed.

The active herbicidal compounds of the present invention may also be used in combination with other herbicides. Such herbicides include, for example: N-(phosphonomethyl) glycine ("glyphosate"); aryloxyalkanoic acids such as (2,4-dichlorophenoxy)acetic acid ("2,4-D"), (4-chloro-2-methylphenoxy)acetic acid ("MCPA"), (+/−)-2-(4-chloro-2-methylphenoxy)propanoic acid (MCPP); ureas such as N,N-dimethyl-N'-[4-(1-methylethyl)phenyl]urea ("isoproturon"); imidazolinones such as 2-[4,5-dihydro-4-methyl-4-(1-methylethyl)-5-oxo-1H-imidazol-2-yl]-3-pyridinecarboxylic acid ("imazapyr"), a reaction product comprising (+/−)-2-[4,5-dihydro-4-methyl-4-(1-methylethyl)-5-oxo-1H-imidazol-2-yl]-4-methylbenzoic acid and (+/−)-2-[4,5-dihydro-4-methyl-4-(1-methylethyl)-5-oxo-1H-imidazol-2-yl]-5-methylbenzoic acid ("imazamethabenz"), (+/−)- 2-[4,5-dihydro-4-methyl-4-(1-methylethyl)-5-oxo-1H-imidazol-2-yl]-5-ethyl-3-pyridinecarboxylic acid ("imazethapyr"), and (+/−)-2-[4,5-dihydro-4-methyl-4-(1-methylethyl)-5-oxo-1H-imidazol-2-yl]-3-quinolinecarboxylic acid ("imazaquin"); diphenyl ethers such as 5-[2-chloro-4-(trifluoromethyl)phenoxy]-2-nitrobenzoic acid ("acifluorfen"), methyl 5-(2,4-dichlorophenoxy)-2-nitrobenzoate ("bifenox"), and 5-[2-chloro-4-(trifluoromethyl)phenoxy]-N-(methylsulfonyl)-2-nitrobenzamide ("fomasafen"); hydroxybenzonitriles such as 4-hydroxy-3,5-diiodobenzonitrile ("ioxynil") and 3,5-dibromo-4-hydroxybenzonitrile ("bromoxynil"); sulfonylureas such as 2-[[[[(4-chloro-6-methoxy-2-pyrimidinyl)amino]carbonyl]amino]sulfonyl]benzoic acid ("chlorimuron"), 2-chloro-N-[[(4-methoxy-6-methyl-1,3,5-triazin-2-yl)amino]carbonyl]benzenesulfonamide ("chlorsulfuron"), 2-[[[[[(4,6-dimethoxy-2-pyrimidinyl)amino]carbonyl]amino]sulfonyl]methyl]benzoic acid ("bensulfuron"), 2-[[[[(4,6-dimethoxy-2-pyrimidinyl)amino]carbonyl]amino]sulfonyl]-1-methyl-1H-pyrazol-4-carboxylic acid ("pyrazosulfuron"), 3-[[[[(4-methoxy-6-methyl-1,3,5-triazin-2-yl)amino]carbonyl]amino]sulfonyl]-2-thiophenecarboxylic acid ("thifensulfuron"), and 2-(2-chloroethoxy)-N-[[(4-methoxy-6-methyl-1,3,5-triazin-2-yl)amino]carbonyl]benzenesulfonamide ("triasulfuron"); 2-(4-aryloxyphenoxy)alkanoic acids such as (+/−)-2-[4-[(6-chloro-2-benzoxazolyl)oxy]phenoxy]propanoic acid ("fenoxaprop"), (+/−)-2-[4-[[5-(trifluoromethyl)-2-pyridinyl]oxy]phenoxy]propanoic acid ("fluazifop"), (+/−)-2-[4-(6-chloro-2-quinoxalinyl)oxy]phenoxy]propanoic acid ("quizalofop"), and (+/−)-2-[-(2,4-dichlorophenoxy)phenoxy]propanoic acid ("diclofop"); benzothiadiazinones such as 3-(1-methylethyl)-1H-2,1,3-benzothiadiazin-4(3H)-one 2,2-dioxide ("bentazone"); 2-chloroacetanilides such as N-butoxymethyl)-2-chloro-2',6'-diethylacetanilide ("butachlor"); arenecarboxylic acids such as 3,6-dichloro-2-methoxybenzoic acid ("dicamba"); and pyridyloxyacetic acids such as [(4-amino-3,5-dichloro-6-fluoro-2-pyridinyl)oxy]acetic acid ("fluroxypyr").

It is apparent that various modifications may be made in the formulation and application of the compounds of this invention without departing from the inventive concepts herein as defined in the claims.

What is claimed is:

1. A compound having the formula:

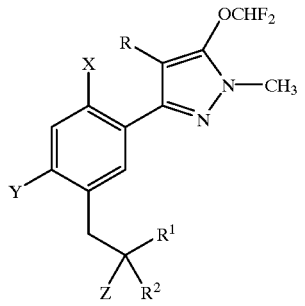

wherein X is H or halogen; Y is halogen, trihaloalkyl or cyano; Z and R are halogen; $R^1$ is carboxyl or agriculturally acceptable salt thereof, cyano, alkoxycarbonyl, alkylthiocarbonyl, alkoxyalkoxycarbonyl, aminocarbonyl, alkylaminocarbonyl, dialkylaminocarbonyl, or alkylsulfonylaminocarbonyl; and $R^2$ is hydrogen or lower alkyl.

2. A compound of claim 1 wherein X is Cl or F; Y is Cl or Br; Z and R are Cl; $R^1$ is cyano, carboxyl or agriculturally acceptable salt thereof, alkoxycarbonyl, alkylthiocarbonyl, alkoxyalkoxycarbonyl, aminocarbonyl, alkylaminocarbonyl, dialkylaminocarbonyl, or alkylsulfonylaminocarbonyl; and $R^2$ is H or methyl.

3. A compound of claim 2 wherein Y is Cl; and $R^2$ is H.

4. A compound of claim 3 wherein $R^1$ is alkoxycarbonyl.

5. A compound of claim 4 wherein X is Cl.

6. A compound of claim 5 wherein $R^1$ is $CO_2CH_2CH_3$.

7. A compound of claim 4 wherein X is F.

8. A compound of claim 7 wherein $R^1$ is $CO_2CH_2CH_3$.

9. An herbicidal composition comprising an herbicidally effective amount of a compound of claim 1, and an agriculturally acceptable carrier therefor.

10. A method of controlling undesired plant growth, comprising application to the locus where the undesired plants are growing or are expected to grow, an herbicidally effective amount of a composition of claim 9.

11. An herbicidal composition comprising an herbicidally effective amount of a compound of claim 1 and an herbicidally effective amount of one or more herbicides selected from the group consisting of glyphosate, 2, 4-D, MCPA, MCPP, isoproturon, imazapyr, imazamethabenz, imazethapyr, imazaquin, acifluorfen, bifenox, fomasafen, ioxynil, bromoxynil, chlorimuron, chlorsulfuron, bensulfuron, pyrazosulfuron, thifensulfuron, triasulfuron, fenoxaprop, fluazifop, quizalofop, diclofop, bentazone, butachlor, dicamba, and fluroxypyr.

12. A method of controlling undesired plant growth, comprising application to the locus where the undesired plants are growing or are expected to grow, an herbicidally effective amount of a composition of claim 11.

13. A process for preparing a compound of claim 1 which comprises the steps of:

a) preparing a mixture of an alkyl nitrite; a copper (II) halide selected from $CuCl_2$ and $CuBr_2$; and an activated olefin selected from the group consisting of $CH_2{=}CHCO_2$-alkyl, $CH_2{=}C(CH_3)CO_2$-alkyl, $CH_2{=}CHCN$, and $CH_2{=}C(CH_3)CN$ in a suitable solvent; and b) treating a compound having the formula:

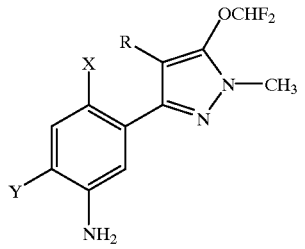

wherein X is H or halogen; Y is halogen, trihaloalkyl or cyano; and R are halogen with the mixture prepared in step a.

* * * * *